United States Patent [19]

Kirkpatrick

[11] 4,066,774

[45] Jan. 3, 1978

[54] METHOD OF KILLING INSECTS EMPLOYING A CERTAIN TRIAZOLE

[75] Inventor: Joel L. Kirkpatrick, Overland Park, Kans.

[73] Assignee: Gulf Oil Corporation, Pittsburgh, Pa.

[21] Appl. No.: 662,171

[22] Filed: Mar. 1, 1976

[51] Int. Cl.$^2$ .............................................. A01N 9/22
[52] U.S. Cl. .................................................. 424/269
[58] Field of Search ......................................... 424/269

[56] References Cited

U.S. PATENT DOCUMENTS 3,308,131   3/1967   McKusick .................. 260/293.63

*Primary Examiner*—V. D. Turner
*Attorney, Agent, or Firm*—Carl A. Cline

[57] ABSTRACT

Insects of the orders Coleoptera and Orthoptera are selectively killed in the presence of living plants by applying to the locus of the insects an effective amount of 1-N,N-dimethylcarbamyl-3-tert.butyl-5-methylthio-1,2,4-triazole.

1 Claim, No Drawings

METHOD OF KILLING INSECTS EMPLOYING A CERTAIN TRIAZOLE

DESCRIPTION OF THE INVENTION a. Background of the Invention

U.S. Pat. No. 3,308,131 discloses a broad class of compounds which are said to be useful as insecticides. Toxicity to mites and aphids is mentioned specifically and in fact it is known that some degree of aphicidal activity is common to most of the specifically disclosed compounds of the class. Miticidal activity of the compounds of the disclosed class is less common and generally of a low order. None of the specifically disclosed compounds in the patent appears to possess adequate efficacy against soil-borne insects combined with sufficiently low mammalian toxicity to meet present day requirements for control of pests such as corn rootworm. Many of the more insecticidal compounds within the disclosed class are highly toxic to mammals (oral $LD_{50}$ values below 5 mg./kg. on laboratory rats).

I have discovered, however, that the compound having the structural formula

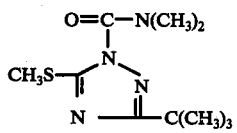

has outstanding properties that are in some aspects inconsistent with the general charcteristics of the disclosed class of compounds. Aside from aphicidal activity, this compound is effective against insects of the orders, Coleoptera and Orthoptera. It is particularly useful in combating the destructive larvae of these insects, including soil-borne pests, in the presence of growing plants. The high degree of efficacy and broad spectrum of insecticidal activity is accompanied by an absence of miticidal activity and an oral $LD_{50}$ on rats of 15 mg./kg.

b. Summary of the Invention

Briefly, my invention is a method of selectively killing insects of the orders Coleoptera and Orthoptera in the presence of living plants comprising applying to the locus of the insects an effective amount of the compound having the structural formula

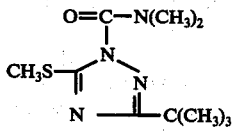

Application to the general area or zone (locus) in which the insects live in either larvae or adult forms is sufficient. It is not necessary to apply the insecticide directly to the insects.

DETAILED DESCRIPTION

The insecticide is conveniently prepared on a laboratory scale by means of the procedures described below.

Preparation of 3-tert.butyl-4H-1,2,4-triazolin-5-thione

To a suspension of 50 g (0.55 mol) of thiosemicarbazide and 43 g (0.05 mol) of pyridine in 300 ml of dioxane was added 42.6 g (0.6 mol) of pivalyl chloride, with cooling. The reaction was stirred at room temperature for 72 hours, then poured into water. The resulting solid was collected, washed with water and dried. The unpurified pivalyl thiosemicarbazide was heated at reflux temperature in 300 ml of 10% sodium hydroxide solution for 3 hours. After cooling, the pH was adjusted to 4 with hydrochloric acid and the product collected, washed with water and dried to give 43.8 g, m.p. 200°–203°. Recrystallization from methanol chloroform gave a sample, m.p. 203°–205°.

Preparation of 3-tert.butyl-5-methylthio-4H-1,2,4-triazole

To a suspension of 40 g (0.254 mol) of 3-tert.butyl-4H-1,2,4-triazolin-5-thione in 300 ml of ethanol, was added 40 g (0.28 mol) of methyliodide. After stirring at room temperature for 16 hrs., the reaction was heated at reflux for two hrs., then was concentrated to near dryness on the rotary evaporator. Water was added to dissolve the resulting solids and the solution was taken to pH 9 with dilute $NH_4OH$. The product precipitated and was collected, giving 32.3 g, m.p. 191°–194° C.

Preparation of 1-Dimethylcarbamyl-3-tert.butyl-5-methylthio-1H-1,2,4-triazole

A solution of 57.6 g (0.338 mol) of 3-tert.butyl-5-methylthio-4H-1,2,4-triazole and 38g (0.355 mol) of dimethylcarbamyl chloride in 300 ml of pyridine was maintained at reflux temperature for 16 hrs. After the pyridine was removed at reduced pressure on the rotary evaporator, water was added followed by chloroform. The organic layer was washed with successive portions of dilute hydrochloric acid, water and brine then dried over $Na_2SO_4$. The solvent was removed in vacuo to give 75 g, $n_D^{26}$ 1.5165 of an oil. Spectral properties agree with the structure IR(film) 5.88μ

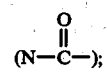

NMR (CDCl₃) (δ1.3(S,9H,t-butyl),2.6(S,3H,—S—CH₃),δ3.13(S,6H,—N(CH₃)₂).

Use of the new insecticide is illustrated by means of controlled tests providing a measure of efficacy on various species, according to procedures described below.

Method for Mites, Aphids, Bean Beetles and Army Worms

Three 5 oz paper cups containing Henderson dwarf lima bean plants and one 5 oz paper cup containing Orange Gem nasturtiums, all growing in vermiculite, are placed on a turntable and sprayed to thorough wetness with 25 ml of a solution of the candidate chemical at the appropriate concentration. Nasturtiums were already infested with 50-100 bean aphids (BA). A bean plant in one paper cup was already infested with 50-100 two-spotted mites (TSM). Leaves from the two remaining bean plants are removed following spraying and placed in disposable petri dishes with 5 southern armyworm (SA) larvae in one petri dish, and 5 Mexican bean beetle (MBB) larvae in the other petri dish. The rating is done approximately 48 hours after spraying as follows:

| BA | TSM |
|---|---|
| 0 = none dead | 0 = no dead adults |
| 1 = 1–25% dead | 1 = 1–25% dead adults |
| 2 = 26–50% dead | 2 = 26–50% dead adults |
| 3 = 51–75% dead | 3 = 51–75% dead adults |
| 4 = 76–100% dead | 4 = 76–99% dead adults |
| 5 = 100% dead | 5 = 100% dead adults |
| MBB | SA |
| 0 = no larvae dead | 0 = no larvae dead |
| 1 = 1–25% larvae dead | 1 = 1–25% larvae dead |
| 2 = 26–50% larvae dead | 2 = 26–50% larvae dead |
| 3 = 51–75% larvae dead | 3 = 51–75% larvae dead |
| 4 = 76–99% larvae dead | 4 = 76–99% larvae dead |
| 5 = 100% larvae dead | 5 = 100% larvae dead |

Method for Southern Corn Rootworm (SCR)

Three 5 oz paper cups planted each with one kernel of DeKalb XL-361 corn are treated two days after planting with 10 ml of a 125 ppm solution of the candidate compound. Compounds with high efficacy are tested at lower concentrations. The experiment is a 4 × 5 factorial in a randomized complete block design with three replications. The tests are evaluated nine days after treatment. The roots are inspected under a dissecting microscope and rated as follows:

| SCR Rating | % root feeding damage |
|---|---|
| 5 | 0 |
| 4 | 1–25 |
| 3 | 26–50 |
| 2 | 51–75 |
| 1 | 76–99 |
| 0 | 100 |

So as to obtain more meaningful results, all tests are performed at the same time of day, whenever possible, usually in the forenoon. Temperature, illumination and humidity are the same in all tests. Atmospheric pressure is not controlled.

Results obtained with the novel insecticide of this invention at various concentrations of active chemical are tabulated below. The ratings given are for averages of three or more replicates. The oral lethal dose for 50 percent kill of laboratory rats is also recorded in the table. In conducting the toxicity tests on rats, 0.01 g of active chemical per ml in corn oil is employed as an additive to the diet of the animals.

| | Insecticidal Use of 1-N,N-Dimethylcarbamyl-3-tert.butyl-5-methylthio-1,2,4-triazole | | | | | |
|---|---|---|---|---|---|---|
| Conc. ppm | Mexican bean beetle | Southern Armyworm | Bean Aphid | Two-Spotted Mites | Corn Rootworm | Remarks |
| 500 | 5 | 1 | 5 | 0 | | |
| 250 | 5 | | 5 | | | |
| 125 | 5 | | 5 | | | Oral |
| 100 | | | | | 5 | $LD_{50}$ 15 mg/kg |
| 62 | 5 | | 5 | | | |
| | 5 | | | | | |
| 50 | | | | | 5 | |
| 31 | 5 | | 5 | | | |
| | 5 | | 5 | | | |
| 25 | | | | | 5 | |
| 15 | 1 | | 5 | | | |
| | 4 | | 5 | | | |
| 12 | | | | | 5 | |
| 8 | | 3 | 5 | | | |
| 6 | | | | | 3.3 | |
| 4 | 0 | | 3 | | | |
| 3 | | | | | 3 | |
| 2 | | | 1 | | | |

It will be realized by workers in the art that the efficacy of the insecticide at low concentration levels makes it advisable to combine the compound with an inert carrier, according to conventional practice. In this way the compound may be distributed more uniformly at desired concentration levels. Water is the most convenient inert carrier in many situations and it is conventional practice to use commercial emulsifiers and dispersing agents so as to easily obtain uniform dispersions in water for spraying. For use against soilborne insects, dry granular combinations of insecticides with solid inert carriers may be preferred, according to the common practice in the art.

It is only necessary to apply the insecticide to the zone in which the insects live, or locus of the insects. Normal activity of the insects will assure adequate contact with the insecticide, so that it need not be applied directly to the insects.

1. The method of selectively killing corn rootworms in the presence of growing corn plants comprising applying to the locus of the corn rootworms an effective amount of 1-N,N-dimethylcarbamyl-3-tert.butyl-5-methylthio-1,2,4-triazole.

* * * * *